United States Patent [19]

Tsuda et al.

[11] 4,260,679
[45] Apr. 7, 1981

[54] METHOD AND REAGENT FOR THE QUANTITATIVE DETERMINATION OF HYDROGEN PEROXIDE AND PRECURSORS THEREOF

[75] Inventors: Mitsuru Tsuda, Mishima; Toshio Tatano, Numazu, both of Japan

[73] Assignee: Kyowa Hakko Kogyo Co., Ltd., Tokyo, Japan

[21] Appl. No.: 62,742

[22] Filed: Aug. 1, 1979

[30] Foreign Application Priority Data

Aug. 1, 1978 [JP] Japan .................................. 53-93835

[51] Int. Cl.³ .......................... C12Q 1/28; C12Q 1/54; C12Q 1/60; C12Q 1/62
[52] U.S. Cl. .................................... 435/10; 23/230 B; 23/901; 23/909; 23/925; 23/932; 435/11; 435/14; 435/28
[58] Field of Search .................... 23/230 B, 925, 932, 23/901, 909; 435/10, 11, 14, 28

[56] References Cited

U.S. PATENT DOCUMENTS

| | | | |
|---|---|---|---|
| 3,630,680 | 12/1971 | Rittesdorf et al. | 23/230 B |
| 3,630,847 | 12/1971 | Rey et al. | 23/230 B X |
| 3,642,444 | 2/1972 | Guehler et al. | 23/230 B |
| 3,979,262 | 9/1976 | Hunziker | 435/28 X |
| 4,089,747 | 5/1978 | Bruschi | 23/230 B X |
| 4,098,574 | 7/1978 | Dappen | 23/230 B X |

FOREIGN PATENT DOCUMENTS

| | | | |
|---|---|---|---|
| 2509156 | 9/1975 | Fed. Rep. of Germany | 23/230 B |
| 2833612 | 2/1979 | Fed. Rep. of Germany | 23/230 B |

*Primary Examiner*—Barry Richman

*Attorney, Agent, or Firm*—Fitzpatrick, Cella, Harper & Scinto

[57] ABSTRACT

A method of and reagent for determining hydrogen peroxide, in which the hydrogen peroxide containing sample is treated with a colouring reagent comprising a peroxidase, a hydrogen donor and an electron or radical acceptor which react stoichiometrically with the hydrogen peroxide to produce a pigment which is then measured colorimetrically. In accordance with the invention the hydrogen donor is specifically a compound of the formula

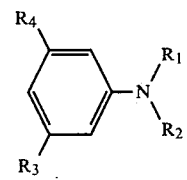

where
$R_1$ is $CH_3$, $C_2H_5$, $CH_2OH$, $CH_2CH_2OH$, $CH_2CH_2NH_2$ or $COCH_3$;
$R_2$ is $CH_2OH$, $CH_2CH_2OH$, $CH_2CH_2NH_2$, $CH_2NHCOCH_3$, $CH_2CH_2NHCOCH_3$ or $COCH_3$;
$R_3$ is H, $CH_3$, $C_2H_5$ or $OCH_3$; and
$R_4$ is H or $CH_3$.

The method and reagent may also be used in the determination of other materials such as cholesterol, phospholipid, glucose and uric acid, by initial treatment with an oxidase thereby quantitatively to produce hydrogen peroxide which is then determined colorimetrically by the method of the invention.

8 Claims, No Drawings

METHOD AND REAGENT FOR THE QUANTITATIVE DETERMINATION OF HYDROGEN PEROXIDE AND PRECURSORS THEREOF

The present invention relates to an improved method for the determination of the amount of hydrogen peroxide and an electron or radical acceptor using a reaction system in which hydrogen peroxide, a hydrogen donor and an electron or radical acceptor are reacted in the presence of peroxidase to form a pigment and a reagent for use therein.

In a widely used method, the quantity of a given compound, e.g. cholesterol, in a sample is determined by treatment of the sample with an oxidase and the amount of hydrogen peroxide formed is measured. Generally hydrogen peroxide is quantitatively determined by a method wherein the hydrogen peroxide is reacted with a colouring agent comprising a peroxidase, a hydrogen donor and an electron or radical acceptor which react together stoichiometrically with the hydrogen peroxide to form a pigement. The amount of hydrogen peroxide is then calculated from the relationship between the amount of the formed pigment and absorbancy at a visible portion of the spectrum.

As the hydrogen donor, the colouring reagent generally contains a compound such as phenol, dimethylaniline, diethylaniline, o-tolidine, o-toluidine, p-toluidine, o-phenylenediamine, N,N'-dimethyl-p-phenylenediamine, benzidine, o-anisidine, p-anisidine, dianisidine, o-cresol, m-cresol, α-naphthol, β-naphthol, catechol, guaiacol, pyrogallol, 2,7-diaminofluorene or leucoindophenol, and as the electron or radical acceptor a compound such as 4-aminoantipyrine, 2-thiophenecarboxylic acid hydrazide, benzidine or 3-methyl-2-benzthiazolinone hydrazone is used.

The conventional method described above has the following defects;

(1) Sensitivity is low in the determination of a trace amount of components.

(2) Formation of pigment is easily affected by components of the sample which may inhibit pigment formation, such as hemoglobin, bilirubin or ascorbic acid.

(3) Stability of coloration after the production of the pigment is low.

Therefore, an improved coloration system is in demand.

In accordance with the present invention, it has been found that improved results are obtained if there is used as the hydrogen donor a compound of the formula

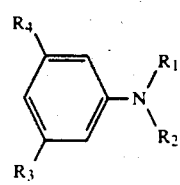

where
$R_1$ is $CH_3$, $C_2H_5$, $CH_2OH$, $CH_2CH_2OH$, $CH_2CH_2NH_2$ or $COCH_3$;
$R_2$ is $CH_2OH$, $CH_2CH_2OH$, $CH_2CH_2NH_2$, $CH_2NHCOCH_3$, $CH_2CH_2NHCOCH_3$ or $COCH_3$;
$R_3$ is H, $CH_3$, $C_2H_5$ or $OCH_3$; and
$R_4$ is H or $CH_3$.

The present invention is based on the principal that the amount of pigment formed in the reaction of hydrogen peroxide with the hydrogen donor and electron or radical acceptor in the presence of peroxidase is directly proportional to the amount of hydrogen peroxide.

In one aspect of the present invention, there is provided a colorimetric reagent for the quantitative determination of hydrogen peroxide in a sample comprising a peroxidase, a hydrogen donor and an electron or radical acceptor, wherein said hydrogen donor is a compound of the formula as hereinbefore define.

In a second aspect of the invention, there is provided a method of quantitatively determining hydrogen peroxide in a sample which comprises treating the sample with a colorimetric reagent comprising a peroxidase, a hydrogen donor and an electron or radical acceptor to form a pigment, and colorimetrically measureing the amount of pigment formed, wherein there is used as the hydrogen donor a compound of the formula defined above.

As the substituted aniline compound used in the present invention as the hydrogen donor, the compounds illustrated in Table 1 may be used. In the compounds in Table 1, Compound No. 28 is a new compound and all other compounds are known compounds. Practical embodiment of preparing Compound No. 28 is illustrated in Example 4 below.

TABLE 1

| Compound No. | $R_1$ | $R_2$ | $R_3$ | $R_4$ |
|---|---|---|---|---|
| 1 | $CH_3$ | $CH_2CH_2OH$ | H | H |
| 2 | " | " | $CH_3$ | H |
| 3 | " | " | " | $CH_3$ |
| 4 | " | " | $C_2H_5$ | H |
| 5 | " | " | $OCH_3$ | H |
| 6 | " | $CH_2CH_2NH_2$ | H | H |
| 7 | " | " | $CH_3$ | H |
| 8 | " | " | " | $CH_3$ |
| 9 | " | " | $C_2H_5$ | H |
| 10 | " | " | $OCH_3$ | H |
| 11 | " | $CH_2CH_2NHCOCH_3$ | H | H |
| 12 | " | " | $CH_3$ | H |
| 13 | " | " | " | $CH_3$ |
| 14 | " | " | $C_2H_5$ | H |
| 15 | " | " | $OCH_3$ | H |
| 16 | $C_2H_5$ | $CH_2CH_2OH$ | H | H |
| 17 | " | " | $CH_3$ | H |
| 18 | " | " | " | $CH_3$ |
| 19 | " | " | $C_2H_5$ | H |
| 20 | " | " | $OCH_3$ | H |
| 21 | " | " | " | $CH_3$ |
| 22 | " | $CH_2CH_2NH_2$ | H | H |
| 23 | " | " | $CH_3$ | H |
| 24 | " | " | $CH_3$ | $CH_3$ |
| 25 | " | " | $C_2H_5$ | H |
| 26 | " | " | $OCH_3$ | H |
| 27 | $C_2H_5$ | $CH_2CH_2NHCOCH_3$ | H | H |
| 28 | " | " | $CH_3$ | H |
| 29 | " | " | $CH_3$ | $CH_3$ |
| 30 | " | " | $C_2H_5$ | H |
| 31 | " | " | $C_2H_5$ | $CH_3$ |
| 32 | " | " | $OCH_3$ | H |
| 33 | " | " | $OCH_3$ | $CH_3$ |
| 34 | $CH_2OH$ | $CH_2CH_2NH_2$ | H | H |
| 35 | " | " | $CH_3$ | H |
| 36 | " | " | $CH_3$ | $CH_3$ |
| 37 | " | " | $C_2H_5$ | H |
| 38 | " | " | $OCH_3$ | H |
| 39 | " | $CH_2NHCOCH_3$ | H | H |
| 40 | " | " | $CH_3$ | H |
| 41 | " | " | " | $CH_3$ |
| 42 | " | " | $C_2H_5$ | H |
| 43 | " | " | $OCH_3$ | H |
| 44 | $CH_2CH_2OH$ | $CH_2CH_2OH$ | H | H |
| 45 | " | " | $CH_3$ | H |
| 46 | " | " | $CH_3$ | $CH_3$ |
| 47 | " | " | $C_2H_5$ | H |

TABLE 1-continued

| Compound No. | R₁ | R₂ | R₃ | R₄ |
|---|---|---|---|---|
| 48 | " | " | OCH₃ | H |
| 49 | " | CH₂CH₂NH₂ | H | H |
| 50 | " | " | CH₃ | H |
| 51 | " | " | CH₃ | CH₃ |
| 52 | " | " | C₂H₅ | H |
| 53 | " | " | OCH₃ | H |
| 54 | " | CH₂CH₂NHCOCH₃ | H | H |
| 55 | " | " | CH₃ | H |
| 56 | " | " | CH₃ | CH₃ |
| 57 | " | " | C₂H₅ | H |
| 58 | " | " | OCH₃ | H |
| 59 | CH₂CH₂NH₂ | CH₂CH₂NHCOCH₃ | H | H |
| 60 | " | " | CH₃ | H |
| 61 | CH₂CH₂NH₂ | CH₂CH₂NHCOCH₃ | CH₃ | CH₃ |
| 62 | " | " | C₂H₅ | H |
| 63 | " | " | OCH₃ | H |
| 64 | " | " | " | CH₃ |
| 65 | COCH₃ | CH₂OH | H | H |
| 66 | " | " | CH₃ | H |
| 67 | " | " | CH₃ | CH₃ |
| 68 | " | " | C₂H₅ | H |
| 69 | " | " | OCH₃ | H |
| 70 | " | CH₂CH₂NH₂ | H | H |
| 71 | " | " | CH₃ | H |
| 72 | " | " | CH₃ | CH₃ |
| 73 | " | " | C₂H₅ | H |
| 74 | " | " | OCH₃ | H |
| 75 | " | COCH₃ | H | H |
| 76 | " | " | CH₃ | H |
| 77 | " | " | CH₃ | CH₃ |
| 78 | " | " | C₂H₅ | H |
| 79 | " | " | OCH₃ | H |

In a particular aspect of the present invention, the above described colorimetric reagent and method are used in the quantitative determination of precursor materials such as cholesterol, which may be converted enzymatically and quantitatively into hydrogen peroxide using an oxidase enzyme. to this end, there may be included in the colorimetric reagent of this invention an oxidase capable of quantitatively converting a precursor material such as cholesterol into hydrogen peroxide, whereby the amount of precursor material present in the original sample may be determined. Correspondingly the present invention also includes a method of determining the amount of precursor material in a sample by treating that precursor material with an oxidase and quantitatively determining the amount of hydrogen peroxide produced by a method as above defined using the compound of formula I as the hydrogen donor.

The method and reagent of this invention may thus be used in the determination of cholesterol, phospholipid, glucose, uric acid, etc. by initial treatment of the sample with an enzyme such as, respectively, a cholesterol oxidase, a choline oxidase, a glucose oxidase, or a uricase followed by colorimetric determination of the hydrogen peroxide used by measuring the visual absorbancy of the sample when subsequently treated with the colouring reagent, i.e. the peroxidase in combination with the hydrogen donor and the electron or radical acceptor.

As the electron or radical acceptor, the conventional materials may be used e.g. 4-aminoantipyrine, 2-thiophenecarboxylic acid hydrazide, benzidine or 3-methyl-2-benzthiazolinone hydrazone.

In the present invention the substituted aniline compound, i.e. the hydrogen donor, is used in an amount enough to react with hydrogen peroxide present or formed in situ in the sample generally 2 to 5 equivalents to hydrogen peroxide. The absorbancy of the coloured solution produced is then measured at a visible portion of 450 to 620 nm and the amount of hydrogen peroxide is calculated from a standard curve for a standard sample.

To illustrate the invention, solutions coloured by the following method using the compounds listed in Table 1 were subjected to the examination of the absorbancy, stability and effect of components in the sample. The results are shown in Table 2.

The test was carried out by adding 0.4 mg of the substituted aniline compound identified in Table 2, 0.6 mg of 4-amino-antipyrine and 30 U of peroxidase to 0.04 mM of hydrogen peroxide solution to make 3 ml of reaction solution. The reaction is illustrated by the following equation.

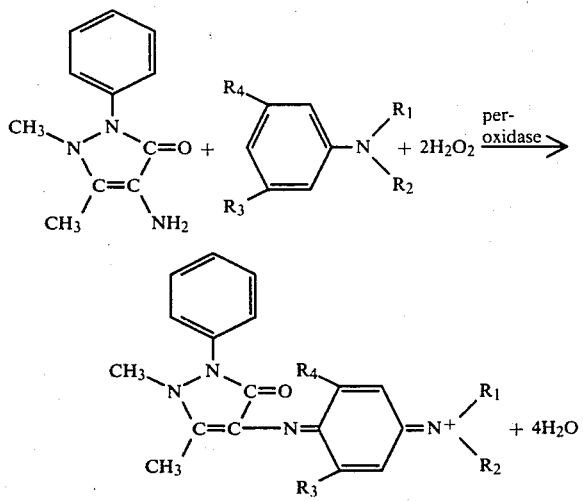

After the reaction, the OD value of the reaction solution at 550 nm was measured and compared with the OD value of phenol used as a hydrogen donor which is defined as 100. Effect of components in the sample is shown by the symbol of "±", "+" and "++", that is, when 4 μg/3 ml of bilirubin or ascorbic acid is present in the sample, "±" means 3 to 6% of effect, "+" means 6 to 20% of effect and "++" means 20% or more of effect. Regarding stability of pigments, "A" means that there is no change in the absorbancy in one hour after coloration, "B" means that the absorbancy at one hour after coloration is reduced and A' means that the absorbancy is reduced after about 10 minutes.

The compounds having higher degree of the absorbancy and higher stability, that is, A in Table 2 are superior as a hydrogen donor.

TABLE 2

| Compound No. | Absorbancy | Effect of inhibiting component | | Stability of coloration |
|---|---|---|---|---|
| | | bilirubin | Vitamine C | |
| 1 | 200 | ± | ± | A |
| 2 | 160 | " | " | B |
| 3 | 70 | " | " | B |
| 4 | 150 | " | " | B |
| 5 | 200 | " | " | A |
| 6 | 150 | " | " | A |
| 7 | 55 | " | " | B |
| 8 | 160 | " | " | A |
| 9 | 45 | " | " | B |
| 10 | 70 | " | " | B |
| 11 | 300 | " | " | A |
| 12 | 320 | " | " | A |
| 13 | 320 | " | " | A |

TABLE 2-continued

| Compound No. | Absorbancy | Effect of inhibiting component bilirubin | Vitamine C | Stability of coloration |
|---|---|---|---|---|
| 14 | 300 | " | " | A |
| 15 | 300 | " | " | A |
| 16 | 200 | " | " | A |
| 17 | 160 | " | " | B |
| 18 | 80 | " | " | B |
| 19 | 190 | " | " | A |
| 20 | 180 | " | " | A |
| 21 | 250 | " | " | A |
| 22 | 70 | " | " | B |
| 23 | 45 | " | " | B |
| 24 | 58 | " | " | B |
| 25 | 75 | " | " | B |
| 26 | 120 | " | " | A |
| 27 | 300 | " | " | A |
| 28 | 350 | " | " | A |
| 29 | 280 | " | " | A |
| 30 | 300 | " | " | A |
| 31 | 200 | " | " | A |
| 32 | 300 | " | " | A |
| 33 | 300 | " | " | A |
| 34 | 150 | " | " | A |
| 35 | 170 | " | " | B |
| 36 | 70 | " | " | B |
| 37 | 130 | " | " | B |
| 38 | 100 | " | " | A |
| 39 | 250 | " | " | A |
| 40 | 340 | " | " | B |
| 41 | 300 | " | " | B |
| 42 | 350 | " | " | B |
| 43 | 230 | " | " | A |
| 44 | 300 | " | " | B |
| 45 | 310 | " | " | B |
| 46 | 300 | " | " | B |
| 47 | 320 | " | " | B |
| 48 | 290 | " | " | B |
| 49 | 150 | " | " | A |
| 50 | 110 | " | " | B |
| 51 | 120 | " | " | A |
| 52 | 180 | " | " | A |
| 53 | 170 | " | " | A |
| 54 | 300 | " | " | B |
| 55 | 350 | " | " | B |
| 56 | 330 | " | " | B |
| 57 | 300 | " | " | B |
| 58 | 260 | " | " | B |
| 59 | 150 | " | " | A |
| 60 | 180 | " | " | B |
| 61 | 150 | " | " | A |
| 62 | 250 | " | " | A |
| 63 | 250 | " | " | A |
| 64 | 170 | " | " | B |
| 65 | 70 | " | " | B |
| 66 | 70 | " | " | B |
| 67 | 68 | " | " | B |
| 68 | 70 | " | " | B |
| 69 | 80 | " | " | B |
| 70 | 60 | " | " | B |
| 71 | 120 | " | " | B |
| 72 | 55 | " | " | B |
| 73 | 65 | " | " | B |
| 74 | 58 | " | " | B |
| 75 | 60 | " | " | B |
| 76 | 70 | " | " | B |
| 77 | 100 | " | " | A |
| 78 | 280 | " | " | A |
| 79 | 70 | " | " | B |
| phenol | 100 | + + | + + | A |
| dimethyl-aniline | 160 | + | ± | A' |
| diethyl-aniline | 180 | + | ± | A' |

The present invention also provides a kit consisting of an oxidase capable of reacting with a precursor material to produce hydrogen peroxide, and a colouring system for quantitatively converting the formed hydrogen peroxide into pigment.

Practical embodiments of the present invention are set forth below. Activity (U) of the enzyme used shows international unit (IU).

EXAMPLE 1

1. Preparation of reagents (1) Enzyme solution

30 U of uricase, 5,000 U of peroxidase, 300 mg of 4-aminoantipyrine and 300 mg of Triton X 100 (i-octyl-phenoxypolyethoxyethanol, Registered Trade Mark and product of Rohm and Haas Co.) are dissolved in 0.1 M sodium-potassium phosphate buffer solution (pH 6.6) to make 300 ml of a solution.

(2) Solution for coloration 600 mg of phenol, 600 mg of dimethylaniline, 600 mg of diethylaniline and 20 mg of m-methyl-(N-ethyl-N'-acetaminoethyl) aniline (Compound No. 28) are dissolved in 30 ml of 0.1 M sodium-potassium phosphate buffer (pH 6.6) solution.

(3) Standard solution 10 mg of uric acid is dissolved in 0.1 M sodium-potassium phosphate buffer (pH 6.6) to make 100 ml of a solution.

2. Method 0.3 ml of the solution for coloration is put into a test tube containing 3 ml of the enzyme solution. 0.02 ml each of five species of serum sample is added to the solution and the mixture is allowed to react at a temperature of 37° C. for 15 minutes. The reaction solution using phenol as the solution for coloration is subjected to colorimetric measurement at 500 nm and the other reaction solution are at 500 nm. Separately, a calibration curve is made from the absorbancy of the standard solution (0.02 ml) and blank values of the reagents. The amount of uric acid in the serum is calculated from the absorbancy and the calibration curve.

The results and control values measured by Uricase-U.V. method are illustrated in Table 3.

TABLE 3

| Serum Sample No. | The amount of uric acid (mg/dl) | | | | |
|---|---|---|---|---|---|
| | Uricase-U.V. method | 1 | 2 | 3 | 4 |
| 1 | 5.5 | 10.2 | 4.3 | 4.2 | 5.5 |
| 2 | 10.6 | 18.5 | 8.5 | 8.8 | 10.5 |
| 3 | 3.0 | 5.7 | 2.5 | 2.4 | 2.9 |
| 4 | 6.1 | 10.0 | 5.7 | 5.5 | 6.2 |
| 5 | 4.3 | 7.1 | 4.1 | 4.6 | 4.3 |

In spite of preciseness the Uricase-U.V. method is not employed in clinical diagnosis because of the complicated process. The results of the present method using Compound No. 28 closely agree with those of the Uricase-U.V. method in precision.

EXAMPLE 2

1. Preparation of reagents (1) Enzyme solution

300 U of cholesterol esterase, 550 U of cholesterol oxidase, 1,700 U of peroxidase, 600 mg of 4-aminoantipyrine and 300 mg of Triton X 100 are dissolved in 0.1 M-trisaminomethanehydrochloric acid buffer solution (pH 6.8) to make exactly 300 ml of a solution.

(2) Solution for coloration 600 mg of phenol, 600 mg of dimethylaniline, 600 mg of diethylaniline, and 25 mg of m-tryl-N,N'-diethanol (Compound No. 45) are dissolved in 30 ml of 0.1M trisaminomethane-hydrochloric acid buffer solution (pH 6.8).

(3) Standard solution 300 mg of cholesterol is dissolved in a solvent of 10 parts of isopropylalcohol, 10 parts of Triton X 100 and 80 parts of distilled water to make exactly 100 ml of a solution.

2. Method 0.02 ml of five species of serum sample is added to a mixture of 3 ml of the enzyme solution and 0.3 ml of the solution for coloration. The mixture is allowed to react at a temperature of 37° C. for 15 minutes. The reaction solution using phenol as the solution for coloration is subjected to colorimetric measurement at 500 nm and the other reaction solutions are at 550 nm. Separately, a calibration curve is made from the absorbancy of the standard solution and blank values of the reagents. The amount of cholesterol in the sample is calculated from the absorbancy and the calibration curve. The results are shown in Table 4 together with the results obtained by gas chromatography.

TABLE 4

| Serum Sample No. | The amount of cholesterol (mg/dl) | | | | |
|---|---|---|---|---|---|
| | Gas Chromatography | 1 | 2 | 3 | 4 |
| 1 | 153 | 163 | 173 | 174 | 151 |
| 2 | 101 | 132 | 130 | 130 | 100 |
| 3 | 78 | 86 | 89 | 88 | 79 |
| 4 | 256 | 278 | 285 | 270 | 254 |
| 5 | 174 | 186 | 190 | 183 | 175 |

EXAMPLE 3

1. Preparation of reagents (1) Enzyme solution

36 U of phospholipase D, 1,000 U of cholineoxidase, 1,800 U of peroxidase, 600 mg of 4-aminoantipyrine, and 300 mg of Triton X 100 are dissolved in 0.1 M sodium-potassium phosphate buffer solution (pH 7.0) to make 300 ml of a solution.

(2) Solution for coloration 600 mg of phenol, 600 mg of dimethylaniline, 600 mg of diethylaniline, and 20 mg of 2-(N-ethyl-m-toluidino) ethanol (Compound No. 17) are dissolved in 30 ml of 0.1 M sodium-potassium phosphate buffer solution (pH 7.0).

(3) Standard solution

Choline chloride is dissolved in an amount of 300 mg as phospholipid in 0.1 M potassium sodium phosphate buffer solution (pH 7.0) to make exactly 100 ml of a solution.

2. method 0.02 ml of serum sample is added to a mixture of 3 ml of enzyme solution and 0.3 ml of a solution for coloraction and the mixture is allowed to react at a temperature of 37° C. for 5 minutes. The reaction solution using phenol as a solution for coloration is subjected to colorimetric measurement at 500 nm and the other reaction solutions are at 550 nm. Separately, a calibration curve is made from the absorbancy of the standard solution (0.02 ml) and blank values of the reagents. The amount of phospholipid in the serum is calculated from the absorbancy and the calibration curve.

The results and control values obtained by Gas-chromatography are shown in Table 5.

TABLE 5

| Serum No. | The amount of phospholipid (mg/dl) | | | | |
|---|---|---|---|---|---|
| | Gas-chromatography | 1 | 2 | 3 | 4 |
| 1 | 148 | 153 | 151 | 155 | 149 |
| 2 | 233 | 238 | 239 | 245 | 233 |
| 3 | 131 | 140 | 148 | 126 | 129 |
| 4 | 179 | 189 | 189 | 187 | 177 |
| 5 | 193 | 210 | 215 | 216 | 194 |

Approximation of the results between the present methods and Gas Chromatography method in Examples 2 and 3 shows accuracy of the present method.

EXAMPLE 4

Preparation of m-methyl-(N-ethyl-N'-acetaminoethyl) aniline (Compound No. 28)

In this Example, 18 g of N-ethyl-N-m-tolylethylenediamine produced by the method described in Japanese Patent Publication No. 11131/70 and 11 g of acetylanhydride are dissolved in a solution of 5 g of sodium acetate in 200 ml of chloroform and the mixture is stirred at room temperature for 3 hours. The reaction mixture is evaporated and the residue is crystallized with methanol to obtain about 18 g of the desired compound. Yield 81%. Physicochemical properties of the compound are as follows.

M.P.: 114.8° C.

U.V. spectrum: 208, 259, 302 nm

IR $\nu_{max}^{cm-1}$ (CHCl$_3$): 1,660, 1,590, 1,500

NMR $\delta$(CDCl$_3$)ppm: 6.66(m,4 H), 5.66(s,1 H), 3.30(m,6 H), 2.20(s,3 H), 1.33(s,3 H), 1.05(t,3 H).

What is claimed is:

1. A colorimetric reagent for the quantitative determination of hydrogen peroxide in a sample comprising a peroxidase, a hydrogen donor and an electron or radical acceptor, wherein said hydrogen donor is a compound of the formula

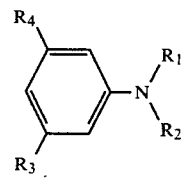

wherein $R_1$ is CH$_3$, C$_2$H$_5$, CH$_2$OH, CH$_2$CH$_2$OH, CH$_2$CH$_2$NH$_2$ or COCH$_3$:

$R_2$ is CH$_2$OH, CH$_2$CH$_2$OH, CH$_2$CH$_2$NH$_2$, CH$_2$NHCOCH$_3$, CH$_2$CH$_2$NHCOCH$_3$ or COCH$_3$;

$R_3$ is H, CH$_3$, C$_2$H$_5$ or OCH$_3$; and $R_4$ is H or CH$_3$.

2. A reagent according to claim 1, wherein the electron or radical acceptor is selected from the group consisting of 4-aminoantipyrine, 2-thiophenecarboxylic acid hydrazide, benzidine and 3-methyl-2-benzthiazolinone hydrazone.

3. A reagent according to claim 1 which additionally contains an oxidase capable of quantitatively forming hydrogen peroxide in situ in a sample from a precursor material, whereby said precursor material may also be quantitatively determined.

4. A reagent according to claim 3, wherein said oxidase is selected from the group consisting of a cholesterol oxidase, a choline oxidase, a glucose oxidase and uricase.

5. A method of quantitatively determining hydrogen peroxide in a sample which comprises treating the sample with a colorimetric reagent comprising a peroxidase, a hydrogen donor and an electron or radical acceptor to form a pigment, and colorimetrically measuring the amount of pigment formed, wherein there is used as the hydrogen donor a compound of the formula defined in claim 1.

6. A method according to claim 5, wherein the electron or free radical acceptor is selected from the group consisting of 4-aminoantipyrine, 2-thiophenecarboxylic acid hydrazide, benzidine and 3-methyl-2-benzthiazolinone hydrazone.

7. A method of quantitatively determining a material in a sample, which comprises treating said sample with an oxidase for said material, thereby to produce hydrogen peroxide in situ and thereafter quantitatively determining the hydrogen peroxide produced, wherein the hydrogen peroxide is determined by a method claimed in claim 5.

8. A method according to claim 7, wherein said material is selected from the group consisting of cholesterol, a phospholipid, a glucose and uric acid and said oxidase is, respectively, selected from the group consisting of a cholesterol oxidase, a choline oxidase, a glucose oxidase and uricase.

* * * * *